United States Patent [19]

Yamada et al.

[11] 4,216,228
[45] * Aug. 5, 1980

[54] COMBATING FUNGI WITH N-BENZYL-N-CYCLOALKYL-UREAS

[75] Inventors: Yasuo Yamada; Junichi Saito; Tatsuo Tamura; Yoshio Kurahashi, all of Tokyo, Japan

[73] Assignee: Bayer Aktiengesellschaft, Leverkusen, Fed. Rep. of Germany

[*] Notice: The portion of the term of this patent subsequent to Nov. 28, 1995, has been disclaimed.

[21] Appl. No.: 916,387

[22] Filed: Jun. 16, 1978

[30] Foreign Application Priority Data

Jul. 12, 1977 [JP] Japan .................................. 52/82602

[51] Int. Cl.² .......................... A01N 9/12; A01N 9/20; C07C 127/15; C07C 157/05
[52] U.S. Cl. ................. 424/322; 260/465 D; 260/552 R; 260/553 A; 260/553 R; 424/304
[58] Field of Search .......... 260/552 R, 553 A, 553 R, 260/465 D; 424/322, 304; 71/120

[56] References Cited

U.S. PATENT DOCUMENTS

| | | | |
|---|---|---|---|
| 3,090,810 | 5/1963 | Berger et al. | 260/552 R |
| 3,483,296 | 12/1969 | Martin et al. | 260/552 R X |
| 3,660,484 | 5/1972 | Martin et al. | 260/552 R |
| 3,683,001 | 8/1972 | Knowles | 260/552 R X |
| 3,701,807 | 10/1972 | Chupp | 260/552 R X |
| 3,761,241 | 9/1973 | Chupp | 260/552 R X |
| 3,829,485 | 8/1974 | Martin et al. | 260/552 R |
| 3,839,440 | 10/1974 | Zecher et al. | 260/553 A |
| 3,927,087 | 12/1975 | Dürr et al. | 260/552 R |
| 4,010,281 | 3/1977 | Yamada et al. | 424/322 |
| 4,036,986 | 7/1977 | Yamada et al. | 260/552 R X |
| 4,127,673 | 11/1978 | Yamada et al. | 260/552 R X |

FOREIGN PATENT DOCUMENTS 644892  7/1962  Canada ............................. 260/552 R

OTHER PUBLICATIONS

Toda et al., CA 69:86500x, (1968).
Kharida et al., Jour. Indian Chem. Soc., vol. 37, No. 11, 1960, pp. 705–709.

Primary Examiner—Thomas A. Waltz
Attorney, Agent, or Firm—Sprung, Felfe, Horn, Lynch & Kramer

[57] ABSTRACT

N-Benzyl-N-cycloalkyl-ureas of the formula

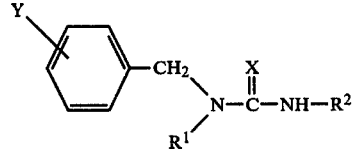

in which
$R^1$ represents cycloalkyl with 5–8 carbon atoms in the ring, which may be optionally substituted by alkyl with 1–8 carbon atoms,
$R^2$ represents alkyl with 1–8 carbon atoms, cycloalkyl with 5–8 carbon atoms in the ring or phenyl,
X represents oxygen or sulphur, and
Y represents halogen, alkyl with 1–8 carbon atoms, cyano or nitro which possess fungicidal properties.

16 Claims, No Drawings

COMBATING FUNGI WITH N-BENZYL-N-CYCLOALKYL-UREAS

The present invention relates to and has for its objects the provision of particular new N-benzyl-N-cycloalkyl-ureas which possess fungicidal properties, active compositions in the form of mixtures of such compounds with solid and liquid dispersible carrier vehicles, and methods for producing such compounds and for using such compounds in a new way especially for combating pests, e.g. fungi, with other and further objects becoming apparent from a study of the within specification and accompanying examples.

It has been disclosed in the published specification of Japanese Patent Application No. 29252/1969 that the compounds of the general formula

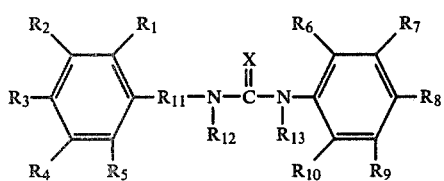
(VI), in which
R$_1$ to R$_{10}$, which need not be identical, each represents hydrogen, halogen, lower alkyl, lower alkoxy or NO$_2$, provided that at least two of R$_1$–R$_5$ and at least two of R$_6$–R$_{10}$ are not hydrogen,
R$_{11}$ is linear alkylene,
R$_{12}$ and R$_{13}$ each represents hydrogen or lower alkyl, and
X represents oxygen or sulphur,
have insecticidal, acaricidal, fungicidal and herbicidal activity.

The present invention now provides, as new compounds, urea and thiourea compounds of the general formula

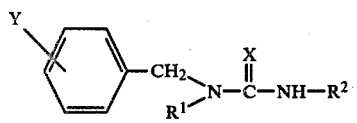
(I)

in which
R$^1$ represents cycloalkyl with 5–8 carbon atoms in the ring, which may be optionally substituted by alkyl with 1–8 carbon atoms,
R$^2$ represents alkyl with 1–8 carbon atoms, cycloalkyl with 5–8 carbon atoms in the ring or phenyl,
X represents oxygen or sulphur, and
Y represents halogen, alkyl with 1–8 carbon atoms, cyano or nitro.

The compounds of the formula (I) have been found to exhibit an excellent fungicidal activity.

Preferably, R$^1$ represents cycloalkyl with 5–7 carbon atoms in the ring (especially cyclopentyl or cyclohexyl), which may be optionally substituted by alkyl with 1–4 carbon atoms (especially methyl); R$^2$ represents ethyl, n-propyl, n-butyl, sec.-butyl, amyl, cyclopentyl, cyclohexyl, cycloheptyl or phenyl; and Y represents chlorine, bromine, cyano, nitro or alkyl with 1–4 carbon atoms (especially methyl). It is especially preferred that Y be in the 4-position.

The invention also provides a process for the preparation of a urea or thiourea compound of the formula (I), in which (a) an N-benzyl-N-cycloalkylamine of the general formula

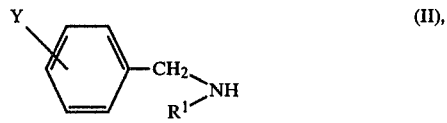
(II), in which
R$^1$ and Y have the meanings stated above,
is reacted with an isocyanate or isothiocyanate of the general formula

$$X=C=N-R^2 \quad (III),$$

in which
R$^2$ and X have the meanings stated above,
or (b) an N-benzyl-N-cycloalkyl carbamoyl (or thiocarbamoyl) halide of the general formula

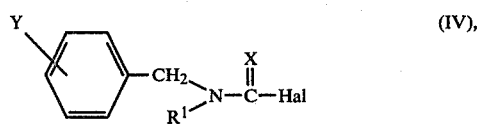
(IV), in which
R$^1$, X and Y have the meanings stated above, and
Hal represents halogen, especially chlorine or bromine,
is reacted with an amine of the general formula

$$H_2N-R^2 \quad (V),$$

in which
R$^2$ has the meaning stated above.

Examples of the N-benzyl-N-cycloalkylamines of the general formula (II), which are used as starting materials in process variant (a), are: N-4-methylbenzyl-N-cyclopentylamine, N-4-methylbenzyl-N-3-methylcyclopentylamine, N-4-methylbenzyl-N-cyclohexylamine, N-4-methylbenzyl-N-2-methylcyclohexylamine, N-4-chlorobenzyl-N-cyclopentylamine, N-4-chlorobenzyl-N-3-methylcyclopentylamine, N-4-chlorobenzyl-N-cyclohexylamine, N-4-chlorobenzyl-N-2-methylcyclohexylamine, N-4-bromobenzyl-N-cyclopentylamine, N-4-bromobenzyl-N-2-methylcyclohexylamine, N-4-cyanobenzyl-N-cyclopentylamine, and N-4-nitrobenzyl-N-chloropentylamine.

Examples of the isocyanates and isothiocyanates of the general formula (III), which are also used as starting materials in process variant (a), are: phenyl isocyanate, phenyl isothiocyanate, cyclopentyl isocyanate, cyclopentyl isothiocyanate, cyclohexyl isocyanate, cyclohexyl isothiocyanate, cycloheptyl isocyanate, cycloheptyl isothiocyanate, ethyl isocyanate, ethyl isothiocyanate, propyl isocyanate, propyl isothiocyanate, butyl isocyanate, butyl isothiocyanate, sec.-butyl isocyanate, sec.-butyl isothiocyanate, amyl isocyanate, and amyl isothiocyanate.

If N-4-methylbenzyl-N-cyclopentylamine and phenyl isocyanate are used as starting materials in process variant (a), the reaction can be illustrated by the following equation.

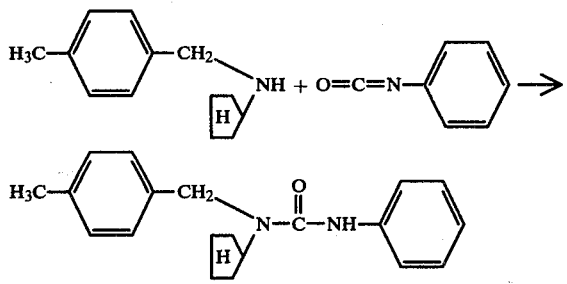

Examples of the N-benzyl-N-cycloalkyl carbamoyl (and thiocarbamoyl) halides of the general formula (IV), which are used as starting materials in process variant (b), are N-4-methylbenzyl-N-cyclopentyl-, N-4-methylbenzyl-N-3-methylcyclopentyl-, N-4-methylbenzyl-N-cyclohexyl-, N-4-methylbenzyl-N-2-methylcyclohexyl-, N-4-chlorobenzyl-N-cyclopentyl-, N-4-chlorobenzyl-N-3-methylcyclopentyl-, N-4-chlorobenzyl-N-cyclohexyl-, N-4-chlorobenzyl-N-2-methylcyclohexyl-, N-4-bromobenzyl-N-cyclopentyl-, N-4-bromobenzyl-N-2-methylcyclohexyl-, N-4-cyanobenzyl-N-cyclopentyl-, and N-4-nitrobenzyl-N-cyclopentyl-carbamoyl (or thiocarbamoyl) chlorides and the corresponding bromides.

Examples of the amines of the general formula (V), which are also used as starting materials in process variant (b), are aniline, cyclopentylamine, cyclohexylamine, cycloheptylamine, ethylamine, propylamine, butylamine, sec.-butylamine, and amylamine.

If N-4-chlorobenzyl-N-cyclopentyl carbamoyl chloride and cyclohexylamine are used as starting materials in process variant (b), the reaction can be illustrated by the following equation:

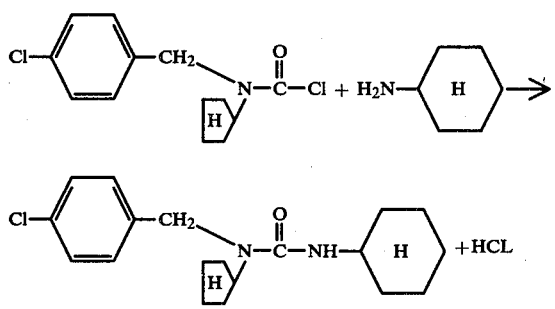

In process variant (b), the reaction may be effected in the presence of an acid-binding agent. Any of the conventional acid acceptors may be used for this purpose, for example an alkali metal hydroxide, an alkali metal carbonate, an alkali metal bicarbonate, an alkali metal alcoholate or a tertiary organic base, for instance triethylamine, dimethylaniline or pyridine.

Process variants (a) and (b) of the present invention are both carried out preferably using a solvent or diluent. Examples of suitable inert solvents or diluents are water and inert organic solvents selected from aliphatic, alicyclic and aromatic hydrocarbons which optionally may be chlorinated, such as hexane, cyclohexane, petroleum ether, ligroin, benzene, toluene, xylene, methylene chloride, chloroform, carbon tetrachloride, ethylene chloride, trichloroethylene and chlorobenzene; ethers, such as diethyl ether, methyl ethyl ether, diisopropyl ether, dibutyl ether, propylene oxide, dioxane and tetrahydrofuran; ketones, such as acetone, methyl ethyl ketone, methyl isopropyl ketone and methyl isobutyl ketone; nitriles, such as acetonitrile, propionitrile and acrylonitrile; alcohols, such as methanol, ethanol, isopropanol, butanol and ethylene glycol; esters, such as ethyl acetate and amyl acetate; acid amides such as dimethyl formamide and dimethyl acetamide; sulfones and sulfoxides, such as dimethyl sulfoxide and dimethyl sulfone; and organic bases, such as pyridine.

Process variants (a) and (b) of the present invention can both be performed over a wide temperature range. In general, the process is carried out at a temperature between −20° C. and the boiling point of the reaction mixture, preferably at a temperature of from 0° to 100° C. Furthermore, the reaction is preferably carried out at atmospheric pressure, although it can also be performed under an elevated or reduced pressure.

The compounds of the formula (I) have an excellent fungicidal activity and a growth-controlling activity against phytopathogenic fungi, and can be used for controlling and eradicating the disease caused by various phytopathogenic fungi. They have a particularly good activity against phytopathogenic fungi from the class Basidiomycetes, which cause, for example, sheath blight in rice plants. The active compounds according to the present invention can be used against parasitic fungi which infect above-ground parts of plants, pathogenic fungi which attack plants through soil to cause tracheomycosis, seed-borne pathogenic fungi and also against soil-borne pathogenic fungi.

These active compounds can be advantageously employed as agricultural and horticultural chemicals for combating fungal diseases of plants, since they show only a low toxicity to warm-blooded animals and have an excellent compatibility with the higher plants, that is to say they do not deleteriously affect cultivated plants at the concentrations usually employed.

Thus, the compounds can be effectively used as fungicides for controlling diseases caused by various phytopathogenic fungi such as Archimycetes, Phycomycetes, Ascomycetes, Basidiomycetes and Fungi Imperfecti.

In particular, the active compounds show remarkable activities against fungi causing sheath blight (*Pellicularia sasakii*) and seedling rot (*Pellicularia filamentosa*), which are serious diseases of rice plants. In addition, the active compounds are effective for the control of the following disease of crop plants: sclerotial blight (*Corticium centrifugum*), blast (*Pyricularia oryzae*), rice bacterial leaf blight (*Xanthomonas oryzae*), Chinese cabbage slimy soft rot (*Erwinia aroideae*), citrus canker (*Xanthomonas citri*), rice heminthosporium leaf spot (*Cochliobolus miyabeanus*), banana leaf spot (*Mycosphaerella musicola*), gray mold of strawberry (*Botrytis cinerea*), grape downy mildew (*Plasmopara viticola*), anthracnose of grape, apple and pear (*Glomella cingulata*), sclerotinia rot of vegetables (*Sclerotinia sclerotiorum*), anthracnose of melons (*Colletotrichum lagenarium*), citrus melanose (*Diaporthe citri*), apple powdery mildew (*Podosphaera leucotricha*), cucumber powdery mildew (*Sphaerotheca fuliginea*), black spot such as apple leaf spot (*Alternaria mali*), potato early blight (*Alternaria solani*) and pear black spot (*Alternaria kikuchiana*), and scab such as apple scab (*Venturia inaequalis*) and pear scab (*Venturia pirina*).

Owing to the excellent fungicidal properties mentioned above, the active compounds according to the present invention can be employed, with good results, against diseases caused by phytopathogenic fungi which hitherto had to be controlled by fungicides containing heavy metals, arsenic or mercury, which are injurious to human beings and domestic animals.

The active compounds can be converted into the customary formulations, such as solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid solvents diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or lactices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The active compounds according to the invention can be present in the formulations as a mixture with other active compounds, such as fungicides, insecticides, acaricides, nematicides, herbicides, bird repellents, growth factors, plant nutrients and agents for improving soil structure.

The formulations in general contain from 0.1 to 95 percent by weight of active compound, preferably from 0.5 to 90 percent.

The active compounds can be used as such, as their formulations or as the use forms prepared therefrom by further dilution, such as ready-to-use solutions, emulsions, suspensions, powders, pastes and granules. They may be used in the customary manner, for example by watering, spraying, atomising, dusting, scattering, dry dressing, moist dressing, wet dressing, slurry dressing or encrusting.

The active compound concentrations in the use forms can be varied within a fairly wide range. They are, in general, from 0.0001 to 20 percent by weight, preferably from 0.005 to 10 percent.

In general, 0.03 to 10 kg, preferably 0.3 to 6 kg, of active compound are employed her hectare of soil surface.

The present invention also provides a fungicidal composition containing as active ingredient a compound of the present invention in admixture with a solid or liquefied gaseous diluent or carrier or in admixture with a liquid diluent or carrier containing a surface-active agent.

The present invention also provides a method of combating fungi which comprises applying to the fungi, or to a habitat thereof, a compound of the present invention alone or in the form of a composition containing as active ingredient a compound of the present invention in admixture with a diluent or carrier.

The present invention further provides crops protected from damage by fungi by being grown in areas in which immediately prior to and/or during the time of the growing a compound of the present invention was applied alone or in admixture with a diluent or carrier.

It will be seen that the usual methods of providing a harvested crop may be improved by the present invention.

The process for the preparation of the compounds of the present invention is illustrated by the following preparative examples:

EXAMPLE 1

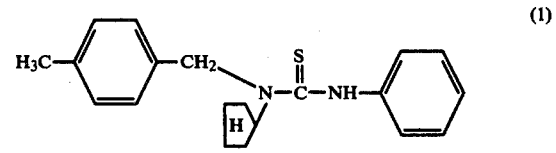

(1)

A solution of 14 g of phenyl isothiocyanate in 50 ml of hexane was added dropwise to 19 g of N-4-methylbenzyl-N-cyclopentyl amine in 400 ml of hexane while cooling and stirring. After the addition, the temperature of the reaction mixture was gradually raised, and the solution was stirred at 40° C. for about 5 hours. The mixture was cooled and filtered. The residue was recrystallized from a mixture of hexane and ethyl alcohol. 30 g of N-4-methylbenzyl-N-cyclopentyl-N'-phenylthiourea were obtained. Melting point: 109°–111° C.

EXAMPLE 2

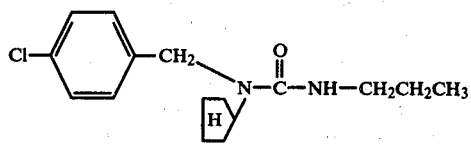  (2)

In a manner analogous to that described in Example 1, 31 g of N-4-chlorobenzyl-N-cyclopentylamine were reacted with 13 g of propyl isocyanate. 32 g of N-4-chlorobenzyl-N-cyclopentyl-N'-propylurea were obtained. Melting point: 103°–105° C.

Other compounds according to the invention which were prepared by methods analogous to those of Examples 1 and 2 are given in Table 1.

Table 1

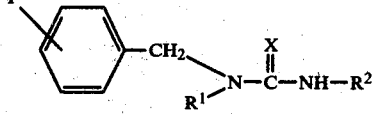  (I)

| Compound No. | R¹ | R² | X | Y | Refractive Index or melting point (°C.) |
|---|---|---|---|---|---|
| 3 | cyclopentyl-H | phenyl | O | 4-CH₃ | 125–127 |
| 4 | H₃C-cyclohexyl-H | phenyl | O | 4-CH₃ | 124–125 |
| 5 | H₃C-cyclohexyl-H | phenyl | S | 4-CH₃ | 55–63 |
| 6 | CH₃-cyclohexyl-H | phenyl | O | 4-CH₃ | 138–139 |
| 7 | CH₃-cyclohexyl-H | phenyl | S | 4-CH₃ | 141–146 |
| 8 | cyclopentyl-H | phenyl | O | 4-CH₃ | 159–160 |
| 9 | cyclopentyl-H | phenyl | S | 4-CN | 85–90 |
| 10 | cyclopentyl-H | phenyl | O | 4-NO₂ | 168–171 |
| 11 | cyclopentyl-H | phenyl | S | 4-NO₂ | 124–129 |
| 12 | cyclopentyl-H | cyclopentyl-H | O | 4-Cl | 91–92 |
| 13 | H₃C-cyclopentyl-H | cyclopentyl-H | O | 4-Cl | 63–73 |
| 14 | CH₃-cyclopentyl-H | cyclopentyl-H | O | 4-Cl | 131–133 |
| 15 | cyclopentyl-H | cyclopentyl-H | O | 4-Br | 95–96 |
| 16 | CH₃-cyclopentyl-H | cyclopentyl-H | O | 4-Br | 127–128 |
| 17 | cyclopentyl-H | cyclohexyl-H | O | 4-Cl | 99–101 |
| 18 | cyclopentyl-H | cyclohexyl-H | S | 4-Cl | 115–120 |
| 19 | cyclopentyl-H | cyclohexyl-H | O | 4-Br | 107–108 |
| 20 | cyclopentyl-H | cyclohexyl-H | S | 4-Br | 123–124 |
| 21 | H₃C-cyclopentyl-H | cyclohexyl-H | O | 4-Cl | 86–88 |
| 22 | CH₃-cyclohexyl-H | cyclohexyl-H | O | 4-Cl | 147–148 |
| 23 | CH₃-cyclohexyl-H | cyclohexyl-H | S | 4-Cl | 135–136 |
| 24 | CH₃-cyclohexyl-H | cyclohexyl-H | O | 4-Br | 140–141 |
| 25 | CH₃-cyclohexyl-H | cyclohexyl-H | S | 4-Br | 131–133 |
| 26 | cyclohexyl-H | cyclohexyl-H | O | 4-Cl | 81–82 |
| 27 | cyclopentyl-H | C₂H₅ | O | 4-Cl | 128–131 |
| 28 | CH₃-cyclohexyl-H | C₃H₇-n | O | 4-Cl | 85–86 |
| 29 | cyclopentyl-H | C₃H₇-n | O | 4-Br | 96–97 |
| 30 | CH₃-cyclohexyl-H | C₃H₇-n | O | 4-CH₃ | 47–54 |
| 31 | cyclopentyl-H | C₄H₉-n | O | 4-Cl | 69–72 |
| 32 | cyclopentyl-H | C₂H₅ | O | 4-Br | 114–115 |
| 33 | H₃C-cyclopentyl-H | C₂H₅ | O | 4-Cl | 88–91 |
| 34 | cyclohexyl-H | C₂H₅ | O | 4-Cl | 88–89 |
| 35 | CH₃-cyclohexyl-H | C₂H₅ | O | 4-Cl | 95–98 |

Table 1-continued $$\text{(I)}$$

Structure: Y-substituted benzyl-CH₂-N(R¹)-C(=X)-NH-R²

| Compound No. | R¹ | R² | X | Y | Refractive Index or melting point (°C.) |
|---|---|---|---|---|---|
| 36 | cyclohexyl (H) | C₂H₅ | O | 4-CH₃ | 77–79 |
| 37 | cyclohexyl-CH₃ (H) | C₂H₅ | O | 4-CH₃ | 62–64 |
| 38 | H₃C-cyclopentyl (H) | C₃H₇-n | O | 4-Cl | 82–84 |
| 39 | H₃C-cyclohexyl (H) | C₃H₇-n | O | 4-CH₃ | $n_D^{20}$= 1.5255 |
| 40 | cyclohexyl (H) | C₃H₇-n | O | 4-CH₃ | 75–76 |
| 41 | cyclopentyl (H) | C₄H₉-n | O | 4-Br | 65–67 |
| 42 | H₃C-cyclopentyl (H) | C₄H₉-n | O | 4-Cl | 53–58 |
| 43 | cyclohexyl (H) | C₄H₉-n | O | 4-Cl | 88–89 |
| 44 | cyclohexyl-CH₃ (H) | C₄H₉-n | O | 4-Cl | 99–101 |
| 45 | cyclohexyl-CH₃ (H) | C₄H₉-n | O | 4-CH₃ | 40–53 |
| 46 | cyclopentyl (H) | C₄H₉-sec | O | 4-Cl | 99–103 |
| 47 | cyclohexyl-CH₃ (H) | C₄H₉-sec | O | 4-Cl | 120–125 |
| 48 | cyclohexyl-CH₃ (H) | C₄H₉-sec | O | 4-Br | 130–133 |
| 49 | cyclohexyl-CH₃ (H) | C₅H₁₁-n | O | 4-Cl | 119–120 |
| 50 | cyclohexyl-CH₃ (H) | C₄H₉-n | S | 4-Cl | 143–145 |
| 51 | cyclohexyl-CH₃ (H) | C₄H₉-n | S | 4-CH₃ | 101–103 |

EXAMPLE 3 (ALTERNATIVE PROCEDURE)

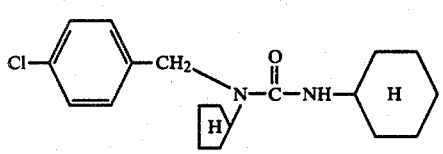

(17)

A solution of 27 g of N-4-chlorobenzyl-N-cyclopentylcarbamoyl chloride in 100 ml of toluene were dropwise added to 20 g of cyclohexylamine in 400 ml of toluene while cooling and stirring. After the addition, the reaction temperature was gradually raised, and the reaction mixture was then stirred at 70°–80° C. for about 10 hours. After cooling, the cyclohexylamine hydrochloride that had been formed was separated by filtration. The toluene layer was washed with water, with 1% aqueous sodium carbonate, with 1% hydrochloric acid, and again with water, and dried over anhydrous sodium sulphate. Then, toluene was distilled off. The residue was recrystallized from a mixture of hexane and ethyl alcohol. 25 g of N-4-chlorobenzyl-N-cyclopentyl-N'-cyclohexylurea was obtained. Melting point: 99°–101° C.

Various fungicidal compositions according to this invention are described in the following examples. The compounds of the present invention are each identified by a number from the preparative examples hereinabove. Parts are by weight.

EXAMPLE 4

A wettable powder was prepared by pulverizing and mixing 50 parts of compound No. 1, 45 parts of a mixture (1:5) of diatomaceous earth and kaolin, and 5 parts of an emulsifier (a polyoxyethylene alkylphenyl ether). This could be diluted with water to a concentration of 0.05% before application by spraying.

EXAMPLE 5

An emulsifiable concentrate was prepared by mixing and stirring 30 parts of compound No. 3, 30 parts of xylene, 30 parts of methylnaphthalene and 10 parts of a polyoxyethylene alkylphenyl ether. This could be diluted with water to a concentration of 0.05% before spraying.

EXAMPLE 6

A dusting agent was prepared by pulverizing and mixing 2 parts of compound No. 21 and 98 parts of a mixture (1:3) of talc and clay. This could be applied by scattering.

EXAMPLE 7

A dusting agent was prepared by pulverizing and mixing 1.5 parts of compound No. 23, 0.5 part of isopropyl hydrogen phosphate (PAP), and 98 parts of a mixture (1:3) of talc and clay.

EXAMPLE 8

10 parts of compound No. 27, 10 parts of bentonite, 78 parts of a mixture (1:3) of talc and clay, and 2 parts of lignin sulfonate were mixed. 25 parts of water were added to the mixture. The whole was mixed thoroughly and then processed with an extrusion granulator into granules of 20 to 40 mesh, which were dried at 40°–50° C.

EXAMPLE 9

95 parts of clay powder having a particle size distribution of 0.2 to 2 mm were placed in a rotary mixer. During rotation, there was sprayed over the particles a solution of 5 parts of compound No. 29 in an organic solvent, thereby wetting them uniformly. Then, drying at 40° to 50° C. was effected in order to form granules.

EXAMPLE 10

An oil preparation was prepared by mixing and stirring 0.5 part of compound No. 30, 20 parts of a high-boiling aromatic compound and 79.5 parts of kerosine.

The fungicidal activity of the compounds of this invention is illustrated by the following biological example.

In this example, the compounds according to the present invention are each identified by a number (given in brackets) from the preparative examples hereinabove:

The known comparison compounds are identified as follows:

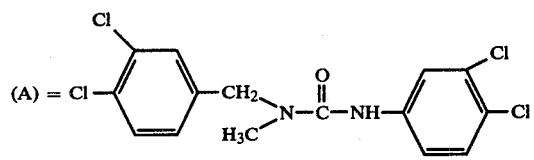

(disclosed in published Japanese Patent Application No. 29252/1969).

(B) = a polyoxine complex (commercially available).
(C) = Bis-(dimethylthiocarbamoylthio)-methyl-arsine

EXAMPLE 11

Test of activity against *Pellicularia sasakii* (sheath blight)/pot test.

Preparation of fungicidal composition:

| Active compound: | 50 parts by weight |
|---|---|
| Carrier: | 45 parts by weight of a mixture (1:5) of diatomaceous earth and kaolin |
| Emulsifier: | 5 parts by weight of polyoxyethylene alkylphenyl ether |

The above-mentioned amounts of the active compound, the carrier and the emulsifier were mixed and ground to form a wettable powder, which was then diluted with water to obtain the prescribed concentration.

Test procedure:

Rice plants (Kinmaze variety) were grown in Wagner pots (0.0002 are) under paddy field conditions. When the rice plant had reached the young ear stage, a liquid preparation, prepared as described above and which contained an active compound in a prescribed concentration, was applied thereto in an amount of 100 ml per three pots.

The day after the active compound was applied, the lower parts of the plants were inoculated with the fungus *Pellicularia sasakii* (which had been grown in a barley medium for 10 days to form its sclerotia). The plants were kept in a greenhouse at a temperature of 28°–30° C. and at a relative humidity of at least 95%. After that, the degree of infection was evaluated, and the phytotoxicity of the active compound was noted. In this evaluation, the extent of the lesion portion spreading from the inoculation point (which was on the lower portion of the plant) was measured, and then the following calculation was made:

$$\text{Degree of infection (\%)} = \frac{3n_3 + 2n_2 + n_1 + n_0}{3N} \times 100$$

in which

N represents the total number of the plant stems observed, $n_0$ represents the number of stems which were not infected, $n_1$ represents the number of stems which were infected over the area extending from the lower portion to the first leaf sheath portion, $n_2$ represents the number of stems which were infected over the area extending from the lower portion to the second leaf sheath portion, and $n_3$ represents the number of stems which were infected over the area extending from the lower portion to the third leaf sheath portion.

The test results are shown in Table 2. The symbol "—" in the final column denotes the absence of observed phytotoxicity; the symbol "±" in the final column denotes some phytotoxicity.

Table 2

Test results against *Pellicularia sasakii*

| Active compound | Concentration of active ingredient (%) | Degree of infection (%) | Phytotoxicity |
|---|---|---|---|
| (1) | 0.0125 | 0 | — |
|  | 0.025 | 0 | — |
|  | 0.05 | 0 | — |
| (2) | 0.0125 | 0 | — |
|  | 0.025 | 0 | — |
|  | 0.05 | 0 | — |
| (3) | 0.0125 | 5.3 | — |
|  | 0.025 | 0 | — |
|  | 0.05 | 0 | — |
| (4) | 0.05 | 11.5 | — |
|  | 0.1 | 2.3 | — |
| (5) | 0.0125 | 7.3 | — |
|  | 0.025 | 0.5 | — |
|  | 0.05 | 0 | — |
| (6) | 0.025 | 9.8 | — |
|  | 0.05 | 0 | — |
| (7) | 0.025 | 5.2 | — |
|  | 0.05 | 0 | — |
| (8) | 0.05 | 20.0 | — |
|  | 0.1 | 10.4 | — |
| (9) | 0.05 | 18.5 | — |
|  | 0.1 | 9.8 | — |
| (10) | 0.05 | 13.3 | — |
|  | 0.1 | 5.7 | — |
| (11) | 0.05 | 7.3 | — |
|  | 0.1 | 0 | — |
| (12) | 0.0125 | 11.2 | — |
|  | 0.025 | 0 | — |
|  | 0.05 | 0 | — |
| (13) | 0.0125 | 9.4 | — |
|  | 0.025 | 0 | — |
|  | 0.05 | 0 | — |
| (14) | 0.025 | 9.0 | — |
|  | 0.05 | 3.5 | — |
| (15) | 0.05 | 12.3 | — |
|  | 0.1 | 7.7 | — |
| (16) | 0.05 | 10.9 | — |
|  | 0.1 | 4.3 | — |
| (17) | 0.0125 | 3.5 | — |
|  | 0.025 | 0 | — |
|  | 0.05 | 0 | — |
| (18) | 0.025 | 7.3 | — |
|  | 0.05 | 0.5 | — |
| (19) | 0.0125 | 9.5 | — |
|  | 0.025 | 0.5 | — |
|  | 0.05 | 0 | — |
| (20) | 0.025 | 7.8 | — |
|  | 0.05 | 0.7 | — |
| (21) | 0.0125 | 0 | — |

Table 2-continued

Test results against *Pellicularia sasakii*

| Active compound | Concentration of active ingredient (%) | Degree of infection (%) | Phytotoxicity |
|---|---|---|---|
| (22) | 0.025 | 0 | — |
|  | 0.05 | 0 | — |
| (23) | 0.0125 | 4.3 | — |
|  | 0.025 | 0 | — |
|  | 0.05 | 0 | — |
| (24) | 0.0125 | 0 | — |
|  | 0.025 | 0 | — |
|  | 0.05 | 0 | — |
| (25) | 0.05 | 15.5 | — |
|  | 0.1 | 7.5 | — |
| (25) | 0.05 | 18.9 | — |
|  | 0.1 | 10.0 | — |
| (27) | 0.025 | 10.3 | — |
|  | 0.05 | 4.1 | — |
| (28) | 0.0125 | 0 | — |
|  | 0.025 | 0 | — |
|  | 0.05 | 0 | — |
| (29) | 0.0125 | 0 | — |
|  | 0.025 | 0 | — |
|  | 0.05 | 0 | — |
| (30) | 0.0125 | 0 | — |
|  | 0.025 | 0 | — |
|  | 0.05 | 0 | — |
| (31) | 0.0125 | 3.7 | — |
|  | 0.025 | 0 | — |
|  | 0.05 | 0 | — |
| (32) | 0.0125 | 5.3 | — |
|  | 0.025 | 0 | — |
|  | 0.05 | 0 | — |
| (33) | 0.0125 | 5.3 | — |
|  | 0.025 | 0 | — |
|  | 0.05 | 0 | — |
| (34) | 0.0125 | 4.7 | — |
|  | 0.025 | 0 | — |
|  | 0.05 | 0 | — |
| (35) | 0.0125 | 0 | — |
|  | 0.025 | 0 | — |
|  | 0.05 | 0 | — |
| (36) | 0.025 | 8.7 | — |
|  | 0.05 | 0 | — |
| (37) | 0.0125 | 0 | — |
|  | 0.025 | 0 | — |
|  | 0.05 | 0 | — |
| (38) | 0.025 | 10.3 | — |
|  | 0.05 | 0.5 | — |
| (39) | 0.0125 | 0 | — |
|  | 0.025 | 0 | — |
|  | 0.05 | 0 | — |
| (40) | 0.025 | 12.5 | — |
|  | 0.05 | 1.0 | — |
| (41) | 0.0125 | 0 | — |
|  | 0.025 | 0 | — |
|  | 0.05 | 0 | — |
| (42) | 0.025 | 3.7 | — |
|  | 0.05 | 0 | — |
| (43) | 0.0125 | 0 | — |
|  | 0.025 | 0 | — |
|  | 0.05 | 0 | — |
| (44) | 0.0125 | 0 | — |
|  | 0.025 | 0 | — |
|  | 0.05 | 0 | — |
| (45) | 0.025 | 14.7 | — |
|  | 0.05 | 9.4 | — |
| (46) | 0.0125 | 3.6 | — |
|  | 0.025 | 0 | — |
|  | 0.05 | 0 | — |
| (47) | 0.0125 | 0 | — |
|  | 0.025 | 0 | — |
|  | 0.05 | 0 | — |
| (48) | 0.0125 | 0 | — |
|  | 0.025 | 0 | — |
|  | 0.05 | 0 | — |
| (49) | 0.05 | 7.3 | — |
|  | 0.1 | 0 | — |
| (50) | 0.0125 | 0 | — |
|  | 0.025 | 0 | — |
| (51) | 0.05 | 0 | — |
|  | 0.0125 | 0 | — |
|  | 0.025 | 0 | — |
|  | 0.05 | 0 | — |
| (A) | 0.05 | 73.5 | — |
|  | 0.1 | 53.0 | — |
| (B) | 0.0045 | 25.7 | — |
| (C) | 0.008 | 2.3 | ± |
| Control | — | 75.4 | — |

It will be appreciated that the instant specification and examples are set forth by way of illustration and not limitation, and that various modifications and changes may be made without departing from the spirit and scope of the present invention.

What we claim is:

1. An N-benzyl-N-cycloalkyl-urea of the formula

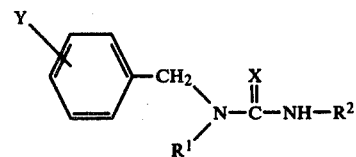

in which
R$^1$ represents cycloalkyl with 5–8 carbon atoms in the ring, which may be optionally substituted by alkyl with 1–8 carbon atoms,
R$^2$ represents alkyl with 1–8 carbon atoms, cycloalkyl with 5–8 carbon atoms in the ring or phenyl,
X represents oxygen or sulphur, and
Y represents alkyl with 1–8 carbon atoms, cyano or nitro.

2. A urea according to claim 1, in which
R$^1$ is cycloalkyl with 5–7 carbon atoms in the ring, optionally substituted by alkyl with 1–4 carbon atoms;
R$^2$ is ethyl, n-propyl, n-butyl, sec.-butyl, amyl, cyclopentyl, cyclohexyl, cycloheptyl or phenyl; and
Y is cyano, nitro or alkyl with 1–4 carbon atoms.

3. A urea according to claim 1, in which Y is in the 4-position.

4. A urea according to claim 1, wherein such urea is N-4-methylbenzyl-N-cyclopentyl-N'-phenylthiourea of the formula

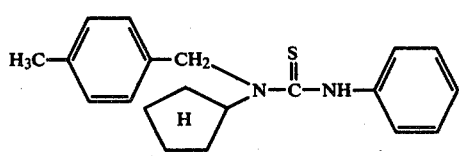

5. A urea according to claim 1, wherein such urea is N-4-chlorobenzyl-N-cyclopentyl-N'-propylurea of the formula

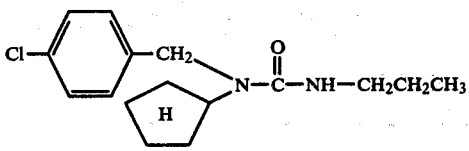

6. A urea according to claim 1, wherein such urea is N-4-chlorobenzyl-N-cyclopentyl-N'-cyclohexylurea of the formula

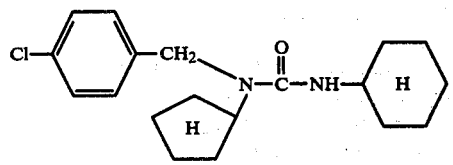

7. A urea according to claim 1, wherein such urea is N-4-chlorobenzyl-N-2-methylcyclohexyl-N'-cyclohexylthiourea of the formula

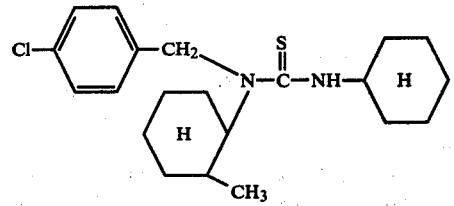

8. A urea according to claim 1, wherein such urea is N-4-bromobenzyl-N-cyclopentyl-N'-propylurea of the formula

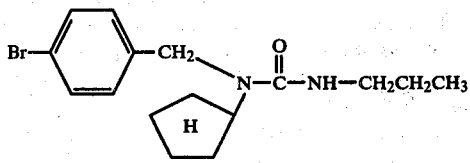

9. A fungicidal composition containing as active ingredient a fungicidally effective amount of a urea according to claim 1 in admixture with a diluent.

10. A method of combating fungi which comprises applying to the fungi, or to a habitat thereof, a fungicidally effective amount of a urea according to claim 1.

11. The method according to claim 10, in which said urea is
N-4-methylbenzyl-N-cyclopentyl-N'-phenylthiourea,
N-4-chlorobenzyl-N-cyclopentyl-N'-propylurea,
N-4-chlorobenzyl-N-cyclopentyl-N'-cyclohexylurea,
N-4-chlorobenzyl-N-2-methylcyclohexyl-N-cyclohexylthiourea or
N-4-bromobenzyl-N-cyclopentyl-N'-propylurea.

12. An N-benzyl-N-cycloalkyl-urea of the formula

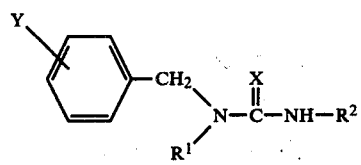

in which
$R^1$ represents cycloalkyl with 5–8 carbon atoms in the ring, which may be optionally substituted by alkyl with 1–8 carbon atoms,
$R^2$ represents alkyl with 1–8 carbon atoms, or cycloalkyl with 5–8 carbon atoms in the ring.
X represents oxygen or sulphur, and Y represents halogen, alkyl with 1–8 carbon atoms, cyano, or nitro.

13. A urea according to claim 12, in which
$R^1$ is cycloalkyl with 5–7 carbon atoms in the ring, optionally substituted by alkyl with 1–4 carbon atoms;
$R^2$ is ethyl, n-propyl, n-butyl, sec.-butyl, amyl, cyclopentyl, cyclohexyl or cycloheptyl; and
Y is cyano, nitro or alkyl with 1–4 carbon atoms.

14. A urea according to claim 12, in which Y is in the 4-position.

15. A fungicidal composition containing as active ingredient a fungicidally effective amount of a urea according to claim 12 in admixture with a diluent.

16. A method of combating fungi which comprises applying to the fungi, or to a habitat thereof, a fungicidally effective amount of a urea according to claim 12.

* * * * *

UNITED STATES PATENT AND TRADEMARK OFFICE
CERTIFICATE OF CORRECTION

PATENT NO. : 4,216,228
DATED : August 5, 1980
INVENTOR(S) : Yasuo Yamada et al

It is certified that error appears in the above-identified patent and that said Letters Patent are hereby corrected as shown below:

Change designation of Assignee from "BAYER AKTIENGESELL-

SCHAFT" to:

-- NIHON TOKUSHU NOYAKU SEIZO K.K., Tokyo, Japan--.

Signed and Sealed this

Fifteenth Day of December 1981

[SEAL]

Attest:

GERALD J. MOSSINGHOFF

Attesting Officer     Commissioner of Patents and Trademarks